(12) United States Patent
Kiick et al.

(10) Patent No.: US 10,172,938 B2
(45) Date of Patent: Jan. 8, 2019

(54) MULTIMODE DEGRADABLE HYDROGELS FOR CONTROLLED RELEASE OF CARGO SUBSTANCES

(71) Applicants: Kristi L. Kiick, Rising Sun, MD (US); April M. Kloxin, Landenberg, PA (US); Prathamesh M. Kharkar, Newark, DE (US); Raja Sivamani, Sacramento, CA (US); Emanual Maverakis, Sacramento, CA (US)

(72) Inventors: Kristi L. Kiick, Rising Sun, MD (US); April M. Kloxin, Landenberg, PA (US); Prathamesh M. Kharkar, Newark, DE (US); Raja Sivamani, Sacramento, CA (US); Emanual Maverakis, Sacramento, CA (US)

(73) Assignees: University of Delaware, Newark, DE (US); The Regents of the University of California, Oakland, CA (US)

( * ) Notice: Subject to any disclaimer, the term of this patent is extended or adjusted under 35 U.S.C. 154(b) by 4 days.

(21) Appl. No.: 15/307,701

(22) PCT Filed: Apr. 28, 2015

(86) PCT No.: PCT/US2015/027942
§ 371 (c)(1),
(2) Date: Oct. 28, 2016

(87) PCT Pub. No.: WO2015/168090
PCT Pub. Date: Nov. 5, 2015

(65) Prior Publication Data
US 2017/0258907 A1    Sep. 14, 2017

Related U.S. Application Data

(60) Provisional application No. 61/984,901, filed on Apr. 28, 2014.

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 41/00* | (2006.01) | |
| *A61K 47/10* | (2017.01) | |
| *A61K 47/34* | (2017.01) | |
| *A61K 47/42* | (2017.01) | |
| *A61K 9/06* | (2006.01) | |
| *C08G 65/333* | (2006.01) | |
| *C08G 65/334* | (2006.01) | |

(52) U.S. Cl.
CPC ............ *A61K 41/0042* (2013.01); *A61K 9/06* (2013.01); *A61K 41/0019* (2013.01); *A61K 47/10* (2013.01); *A61K 47/34* (2013.01); *A61K 47/42* (2013.01); *C08G 65/3344* (2013.01); *C08G 65/33327* (2013.01); *C08G 2210/00* (2013.01); *C08G 2650/04* (2013.01)

(58) Field of Classification Search
CPC .... A61K 41/0042; A61K 47/34; A61K 47/10; A61K 9/06; C08G 65/3344; C08G 2210/00; C08G 65/33327; C08G 650/04
See application file for complete search history.

(56) References Cited

U.S. PATENT DOCUMENTS

| 4,188,340 A | 2/1980 | Hickner | |
| 2013/0244975 A1* | 9/2013 | Baldwin et al. | ............................ A61K 47/48215 514/56 |
| 2014/0031285 A1* | 1/2014 | Anseth | .................... A61K 47/34 514/8.9 |
| 2015/0267196 A1* | 9/2015 | Alsberg | .................. C08L 29/04 514/44 A |

FOREIGN PATENT DOCUMENTS

WO    2014059446    4/2014

OTHER PUBLICATIONS

Kloxin, A.M., et al., "Photodegradable hydrogels for dynamic tuning of physical and chemical properties," Apr. 3, 2009, pp. 59-63, vol. 324(5923), Science.
International Search Report and Written Opinion for International Application No. PCT/US2015/027942, dated Jul. 20, 2015, 11 pages.
International Preliminary Report on Patentability and Written Opinion for International Application No. PCT/US2015/027942, dated Nov. 1, 2016, 9 pages.
Meng, L.L., et al., "Chitosan-based nanocarriers with pH and light dual response for anticancer drug delivery," Jul. 2, 2013, pp. 2601-2610, vol. 14(8), Biomacromolecules.
Kloxin, A.M., et al., "Synthesis of photodegraclable hydrogels as dynamically tunable cell culture platforms," Nov. 4, 2010, pp. 1867-1887, vol. 5(12), Nature Protocols.
Baldwin, A.D., et al., "Reversible maleimide-thiol adducts yield glutathione-sensitive poly(ethylene glycol)-heparin hydrogels," Sep. 11, 2012, pp. 133-143, vol. 4(1), Polymer Chemistry.

* cited by examiner

*Primary Examiner* — Jessica Whiteley
(74) *Attorney, Agent, or Firm* — RatnerPrestia

(57) ABSTRACT

A responsive hydrogel-based material may be used as a carrier system for the in situ delivery of various cargo substances, including bioactive moieties. The hydrogel structure, which includes photodegradable and thioether moieties in its three dimensional network, enables finely tuned local release of cargo substances as a function of the in vivo tissue environment (e.g., enzyme concentration or reducing environment) and externally applied stimuli (e.g., light) by selective spatiotemporal hydrogel degradation.

34 Claims, 4 Drawing Sheets

MULTIMODE DEGRADABLE HYDROGELS FOR CONTROLLED RELEASE OF CARGO SUBSTANCES

CROSS-REFERENCE TO RELATED APPLICATION

This application is the U.S. National Phase Application of PCT/US2015/027942, filed Apr. 28, 2015, which claims priority to U.S. Provisional Application No. 61/984,901, filed Apr. 28, 2014. The disclosure of each of these applications is incorporated herein by reference in its entirety for all purposes.

FEDERAL FUNDING

This invention was made with federal funding under Grant No. P20RR017716 awarded by the National Institutes of Health. The U.S. government has certain rights in the invention.

FIELD OF THE INVENTION

The invention pertains to degradable hydrogels useful for the controlled release of cargo substances (such as bioactive agents) as well as reactants and methods for preparing such hydrogels and compositions containing cargo substances encapsulated and/or bound within the hydrogels. The present invention provides the ability to control on demand the release of cargo substances such as drugs and proteins in situ by multiple modes of hydrogel degradation as a function of, for example, enzyme concentration, reducing conditions, hydrolysis, and/or externally applied light.

DISCUSSION OF THE RELATED ART

Efficient and effective delivery of many hydrophobic and hydrophilic molecules, such as small molecule drugs and proteins, respectively, is a major challenge in the field of therapeutic delivery. In addition, control over the spatial and temporal release of cargo molecules from the carrier system is critical in the reduction of potential side effects, as well as the cost associated with various cargo molecules. Further, the delivery and release of mammalian cells in cell-based therapies requires control of the physical, chemical and biological properties of the environment surrounding the cells (i.e., the delivery vehicle) to main cell viability and function and to facilitate cellular processes, such as migration, differentiation and protein secretion.

Different types of nanoparticles and microparticles, including liposomes and polymersomes, as well as various hydrogel-based carriers have been developed for use in controlled biomolecule delivery. However, particles require targeting for localized release and most materials for controlled release typically have only a single programmed release rate or mode of release. Thus, the development of new carrier systems that offer the ability to control the release of cargo molecules in situ and on demand by multiple modes of hydrogel degradation in response to enzyme concentration, reducing environment, hydrolysis and/or externally applied light would be of great interest.

SUMMARY OF THE INVENTION

One aspect of the invention provides a hydrogel comprising a three-dimensional network of polymeric segments, wherein the polymeric segments are linked together, at least in part, by at least one photodegradable moiety and at least one thioether-containing moiety obtained by reaction of a thiol (e.g., an arylthiol) with an α,β-unsaturated carbonyl functional group (e.g., a maleimide). As used herein, the term "photodegradable moiety" means a group containing one or more bonds that break (cleave) in response to exposure to radiation of the appropriate wavelength and energy.

The hydrogel may, in one embodiment of the invention, comprise a first polymeric segment coupled to a second polymeric segment through a multimode degradable linkage comprised of a photodegradable moiety and a thioether-containing moiety obtained by reaction of a thiol with an α,β-unsaturated carbonyl functional group. The multimode degradable linkage may be additionally comprised of a hydrolyzable moiety, such as an ester or amide moiety.

The polymeric segments may be based on any type of natural, naturally derived or synthetic polymer, including for example, polyethers (e.g., polyethylene glycols), polysaccharides, polypeptides (including proteins), poly(meth)acrylates, polyvinyl alcohols, PLA, PGLA and the like and combinations thereof. In one embodiment, the polymeric segments include polyoxyalkylene-containing segments. In another embodiment, the polymeric segments include polymeric segments selected from the group consisting of polyether-containing segments, polypeptide-containing segments and polysaccharide-containing segments. A bioactive substance may be covalently bound into the three-dimensional network of the hydrogel.

The at least one photodegradable moiety may, in one embodiment of the invention, include at least one photodegradable moiety selected from the group consisting of nitro-substituted benzyl ester moieties and nitro-substituted benzyl amide moieties. In a further aspect of the invention, the at least one photodegradable moiety includes at least one photodegradable moiety containing an ester or amide linkage in the backbone of the three-dimensional network that undergoes irreversible cleavage upon being irradiated with UV, visible or IR light.

In one embodiment, the at least one photodegradable moiety includes at least one photodegradable moiety having the general structure —Ar(NO$_2$)—CHR'—Z—C(=O)—, wherein Ar is an aromatic moiety (e.g., a benzene ring) substituted with a nitro group ortho to —CHR'—, Z is O or NH, and R' is H or alkyl (e.g., C1-C6 alkyl, such as methyl). The aromatic moiety may optionally be substituted with one or more substituents other than the nitro group, such as an alkoxy group meta to —CHR'—.

The polymeric segments of the hydrogel may be additionally linked together by at least one hydrolyzable moiety, e.g., an enzymatically-hydrolyzable moiety or an ester or amide moiety.

The thioether-containing moiety or moieties present in the hydrogel may be obtained by reaction of a thiol (e.g., an aryl thiol or an aliphatic thiol) with an α,β-unsaturated carbonyl functional group (e.g., a maleimide functional group). The thioether-containing moiety may be capable of undergoing thiol exchange, wherein a thioether linkage in the backbone of the hydrogel is cleaved in accordance with the following general scheme:

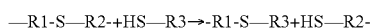

Thioether Thiol
Linkage

The net result of such a thiol exchange is scission of a linkage in the hydrogel network. Without wishing to be bound by theory, it is believed that the thiol exchange may be proceeding by way of a retro Michael-type addition (wherein the thioether reverts to the thiol and α,β-unsaturated carbonyl, with the α,β-unsaturated carbonyl thus generated being intercepted by a second thiol).

For example, the thioether-containing moiety capable of undergoing a thiol exchange reaction may have the structural formula -A-S—R— where A is an aryl moiety or a heteroaromatic ring moiety and R is a succinimide moiety (the S being covalently bound to a carbon atom of the succinimide moiety, i.e., a carbon atom alpha to a carbonyl group in the succinimide moiety).

In one embodiment of the invention, the polymeric segments of the hydrogel are linked together, at least in part, by at least one moiety comprising structure (II):

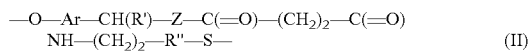
(II)

wherein Ar is a nitro-substituted aromatic ring, R' is H or alkyl (e.g., C1-C6 alkyl, such as methyl), Z is O or NH, R" is a succinimide moiety having a nitrogen atom covalently bonded to —(CH$_2$)$_2$—, and S is covalently bound to R" through a carbon atom of the succinimide moiety (i.e., a carbon atom alpha to a carbonyl group in the succinimide moiety).

In another embodiment of the invention, the polymeric segments of the hydrogel are linked together, at least in part, by at least one moiety comprising structure (III):

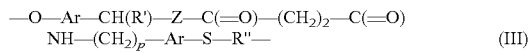
(III)

wherein Ar is a nitro-substituted aromatic ring, R' is H or alkyl (e.g., C1-C6 alkyl, such as methyl), Z is O or NH, Ar' is an aromatic ring, p is an integer of 1 or more (e.g., 1 to 4), R" is a succinimide moiety, and S is covalently bound to R" through a carbon atom of the succinimide moiety (i.e., a carbon atom alpha to a carbonyl group in the succinimide moiety).

The present invention also provides compositions comprising a hydrogel in accordance with the invention with at least one cargo substance encapsulated therein and/or covalently bound to the three-dimensional network of the hydrogel. The cargo substance may be a bioactive substance, for example, such as a bioactive substance selected from the group consisting of small molecule drugs, biomolecules, biomacromolecules and cells. The bioactive substance may be supported on a non-bioactive carrier. The cargo substance may be a polymeric or inorganic particle. In certain embodiments of the invention, the cargo substance is physically retained within the hydrogel, while in other embodiments the cargo substance is covalently bound to the hydrogel.

Further provided by the present invention is a method of delivering a cargo substance to a subject in need thereof, wherein the method comprises administering a composition in accordance with any embodiment of the invention as described herein to the subject. The composition may be administered topically or by injection or implantation, for example. The method may additionally comprise exposing at least a portion of the composition to light following administration of the composition to the subject.

A method of making a hydrogel is further provided by the present invention, wherein the method comprises reacting a functionalized polymer bearing at least x functional groups X with a functionalized linker molecule bearing at least y functional groups Y, wherein a) x and y are each independently an integer of 2 or more and x+y is an integer of 5 or more; b) X and Y are different from each other and are selected from the group consisting of α,β-unsaturated carbonyl and thiol; c) at least one of the functionalized polymer or the functionalized linker molecule has a backbone containing at least one photodegradable moiety; and d) X and Y react to form a thioether linkage. The functionalized polymer may be a functionalized polyether, functionalized polypeptide or functionalized polysaccharide, for example. The functionalized linker molecule may also be a functionalized polyether, functionalized polypeptide or functionalized polysaccharide, in one aspect of the invention. In another embodiment, the linker molecule may be a functionalized bioactive substance (e.g., a thiol-functionalized protein or peptide). The at least one photodegradable moiety may include at least one photodegradable moiety containing an ester or amide linkage that undergoes irreversible cleavage upon being irradiated with UV, visible or IR light. For example, the photodegradable moiety may include at least one photodegradable moiety selected from the group consisting of nitro-substituted benzyl moieties.

X and Y, in one aspect of the invention, may be selected from the group consisting of maleimide and arylthiol. The functionalized linker molecule may be, for example, a polyether, polypeptide or polysaccharide bearing at least y functional groups Y.

In further exemplary embodiments of the invention, the functionalized polyether or the functionalized linker molecule used to prepare the hydrogel corresponds to structure (I):

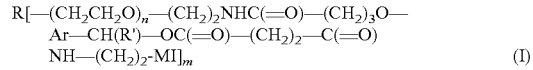
(I)

wherein R is an organic moiety, n is an integer of 2 or more (e.g., 2 to 100), Ar is a nitro-substituted aromatic ring, R' is H or alkyl (e.g., C1-C6 alkyl, such as methyl), MI is a maleimide moiety having a nitrogen atom covalently bonded to —(CH$_2$)$_2$— and m is an integer of 2 or more (e.g., 2, 3, 4, 5, 6, etc.). A maleimide-functionalized macromer of structure (I) may be reacted, for example, with a multi-arm thiol-functionalized polyether (which may or may not contain one or more photodegradable moieties) to form a hydrogel.

In other embodiments of the invention, the functionalized polyether or the functionalized linker molecule used to prepare the hydrogel has structure (IV):

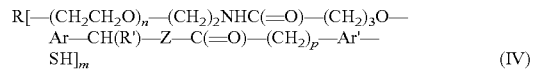
(IV)

wherein R is an organic moiety, n is an integer of 2 or more (e.g., 2 to 100), Ar is a nitro-substituted aromatic ring, R' is H or alkyl (e.g., C1-C6 alkyl, such as methyl), Z is O or NH, Ar' is an aromatic ring (e.g., a benzene ring), p is an integer of 1 or more (e.g., 1, 2, 3, 4, 5, 6, etc.), and m is an integer of 2 or more (e.g., 2, 3, 4, 5, 6, etc.).

To prepare a hydrogel, a thiol-functionalized macromer of structure (IV) may be reacted with a multi-arm maleimide-functionalized polyether (wherein the maleimide-functionalized polyether may or may not contain one or more photodegradable moieties).

A still further aspect of the invention provides a functionalized polyether having structure (I):

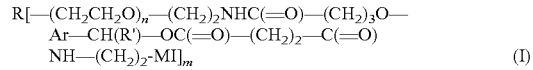
(I)

wherein R is an organic moiety, n is an integer of 2 or more (e.g., 2 to 100), Ar is a nitro-substituted aromatic ring, R' is H or alkyl (e.g., methyl), MI is a maleimide moiety having a nitrogen atom covalently bonded to —(CH$_2$)$_2$— and m is an integer of 2 or more (e.g., 2, 3, 4, 5, 6, etc.).

Also provided in one embodiment of the invention is a functionalized polyether having structure (IV):

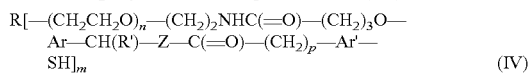

wherein R is an organic moiety, n is an integer of 2 or more (e.g., 2 to 100), Ar is a nitro-substituted aromatic ring, R' is H or alkyl (e.g., methyl), Z is O or NH, Ar' is an aromatic ring, p is an integer of 1 or more (e.g., 1, 2, 3, 4, 5, 6 etc.), and m is an integer of 2 or more (e.g., 2, 3, 4, 5, 6, etc.).

DETAILED DESCRIPTION OF THE INVENTION

Hydrogels

Figure 1:
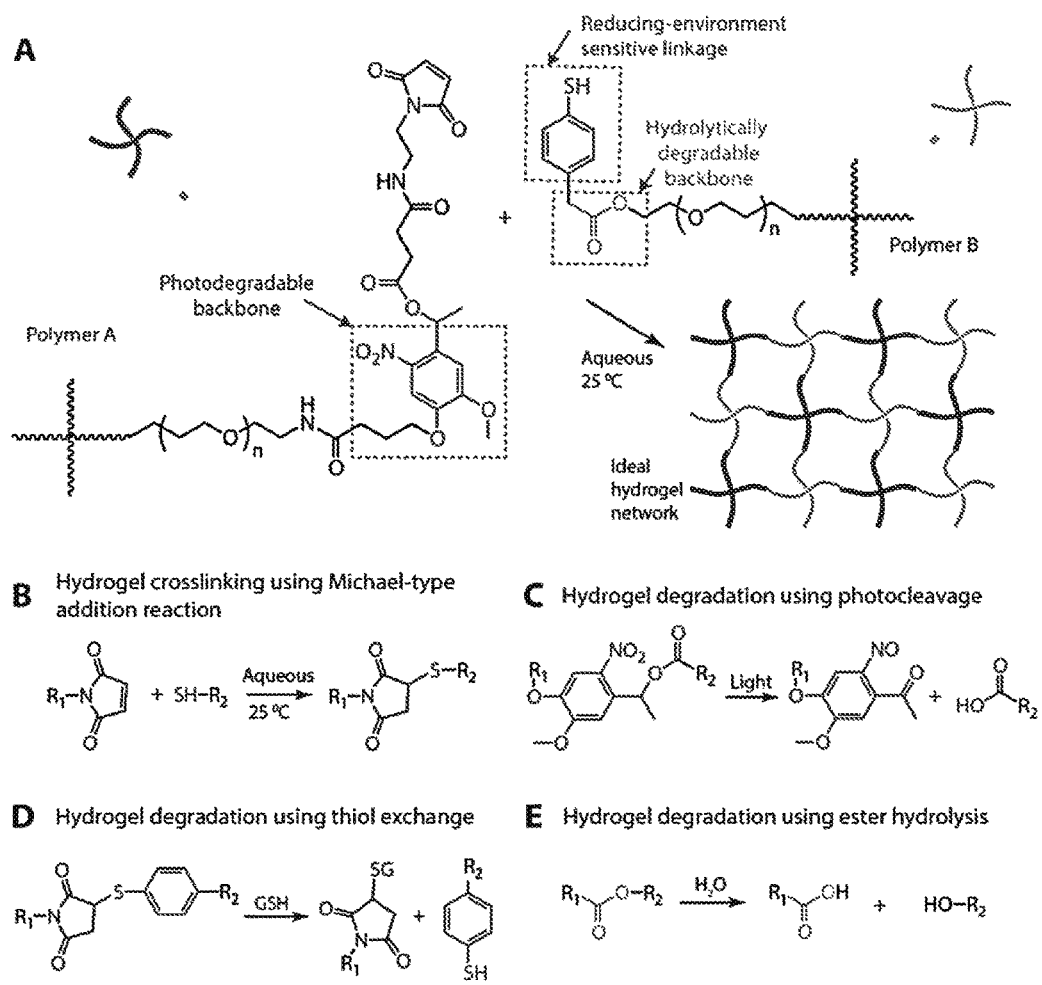
FIG. 1 shows, in schematic form, the preparation of an illustrative, exemplary hydrogel in accordance with the invention, as well as potential mechanisms by which such hydrogel can degrade.

Hydrogels in accordance with the present invention may be characterized as three-dimensional networks of polymeric segments. That is, the polymeric segments form a cross-linked network within which cargo substances can be retained, either by physical entrapment or by molecular interaction (non-covalent affinity, e.g., ionic interactions, hydrogen bonding, complexation) or by covalent bonding or any combination thereof. The linkages between the polymeric segments may define openings in the network, the size of which may hinder or prevent encapsulated cargo substances from being released from the network until such time as the hydrogel undergoes degradation by one or more mechanisms. The polymeric segments are linked together, at least in part, by at least one photodegradable moiety and at least one thioether-containing moiety obtained by reaction of a thiol with an α,β-unsaturated carbonyl functional group. An individual linkage between a first polymeric segment and a second polymeric segment may contain both at least one photodegradable moiety and at least one thioether-containing moiety. The thioether-containing moiety may be capable of undergoing degradation via a retro Michael-type addition reaction and/or a thiol exchange reaction. One or more other types of degradable moieties may additionally be present in the hydrogel, such as, for example, a hydrolyzable group such as an ester or amide group (the hydrolyzable group may be an enzymatically-hydrolyzable group, for instance). As will be explained in more detail subsequently, the aforementioned moieties may be present in the backbone of one or more of the interlinked polymeric segments comprising the hydrogel and/or in linkages between the hydrogel network and cargo substances pendant thereto. Upon exposure to an appropriate stimulus (such as light, in the case of a photodegradable moiety), the moiety may undergo cleavage or scission, thereby leading to breakdown of the three dimensional network structure of the hydrogel and/or degradation of the linkage between the cargo substance and the hydrogel and release of a cargo substance initially trapped or bound within that network. The hydrogels of the present invention thus may be designed to be capable of undergoing degradation by two or more mechanisms, including, for example, 1) cleavage of thioether linkages by retro Michael-type addition reactions and/or thiol exchange reactions, 2) cleavage of photodegradable linkages through exposure to light and 3) ester and/or amide hydrolysis (which may be catalyzed by enzymes).

The polymeric segments, which typically comprise most of the structure of the hydrogel, are preferably selected such that the hydrogel is cytocompatible. Cytocompatibility, as defined herein, means that the hydrogel is not cytotoxic to desired cells. Additionally, it is preferred that the polymeric segments present in the hydrogel are selected such that the hydrogel is biocompatible. Biocompatible, as defined herein, means that a hydrogel does not cause a significant immunological and inflammatory response if placed in vivo for tissue regeneration and is preferably biodegradable, affording non-toxic species.

In one aspect of the invention, the polymeric segments incorporated into the hydrogel are hydrophilic in character and contain chains of repeating units which in non-cross-linked form are water soluble. For example, the polymeric segments may be polyether-containing segments, in particular polyoxyalkylene-containing segments such as polyoxyethylene-containing segments, polyoxypropylene-containing segments, mixed polyoxyethylene/polyoxypropylene-containing segments, polyoxytetramethylene-containing segments and the like and combinations thereof. In one embodiment of the invention, the backbone of the hydrogel contains segments having structure —(CH$_2$CH$_2$O)$_n$—, wherein n may be an integer of from 2 to 200 (e.g., 25 to 150) for example (although in principle n could be much greater than 200). Polysaccharide-containing and polypeptide-containing segments may also be employed as polymeric segments in the hydrogels of the present invention. For example, suitable polysaccharide-containing segments may be based on alginates, agaroses, carrageenans, dextrans or glycosaminoglycans such as chitosan, heparin or hyaluronic acid. Proteins, including fibrin, albumin and collagen for example, may provide the basis of polypeptide-containing segments in the hydrogel. As used herein, the term "polypeptide" refers to chains of amino acids, of any molecular weight, linked together by peptide bonds. The polymeric segments may be based on any other known type of polymer, both natural and synthetic, including for example polyacrylates, polymethacrylates (including poly(hydroxyethyl) methacrylates), polyvinyl alcohols, polyacrylamides, polyphosphazenes, poly(lactic-co-glycolic acid) (PLGA), PGA (polyglycolic acid), PLA (polylactic acid), polycaprolactones, polyamides, poly(ethyloxazolines), poly(vinylpyrrolidones) and the like and combinations thereof.

The molecular weights of the polymeric segments linked together to form hydrogels in accordance with the present invention may be selected so as to impart desired characteristics to the hydrogel, such as the size of the openings in the hydrogel network. Generally speaking, when the reactive functional groups used to link the polymeric segments together are at terminal positions, higher molecular weights will lead to larger sized openings. Typically, the molecular weights of the polymeric segments may range from 500 to 50,000 daltons, for example. Polymeric segments of different molecular weight may be present in the hydrogel network.

The polymeric segments may be linear and/or branched. For example, in the embodiment where the polymeric segments are comprised of polyoxyethylene segments, an individual polyoxyethylene segment may correspond to the linear structure —(CH$_2$CH$_2$O)$_n$—, wherein n may be an integer of 2 or more (e.g., from 2 to 200 or 50 to 150) or to the branched structure R—[—(CH$_2$CH$_2$O)$_n$]$_m$—, wherein n is an integer of at least 1 (e.g., 1 to 100 or 25 to 100), m is an integer of 3 or more (e.g., 3, 4, 5, 6, etc.), and R is a polyvalent organic moiety (e.g., a glycerol, sugar, sugar alcohol or pentaerythritol residue).

As previously mentioned, the polymeric segments are linked together, at least in part, by at least one type of photodegradable moiety and at least one type of thioether-containing moiety obtained by reaction of a thiol with an α,β-unsaturated carbonyl functional group (which may or may not be degradable, such as by a retro Michael-type addition and thiol exchange reaction). However, the polymeric segments may additionally be linked together through other types of moieties, which may be either degradable or non-degradable. For example, the hydrogel may additionally contain ester and/or amide linkages capable of being degraded through hydrolysis (e.g., enzymatically-catalyzed hydrolysis).

In the context of the present invention, a degradable linkage is a covalent linkage between polymeric segments and/or between a polymeric segment and a cargo substance which is capable of being cleaved when exposed to a stimulus, which may be either endogenous or exogenous (e.g., present in the environment surrounding the hydrogel or applied externally and on demand). Following such cleavage, the polymeric segments are no longer covalently attached to each other and/or the cargo substance is no longer attached to the hydrogel network. Such degradation results in the three dimensional network of the hydrogel being converted into smaller fragments and/or in openings in the hydrogel being made larger and/or in release of a bound cargo substance from the hydrogel network. As an example, a hydrogel containing two o-nitro benzyl-containing photodegradable moieties linking polymeric segments "PS1", "PS2" and "PS3" may undergo cleavage following exposure of the hydrogel to light as shown schematically in the following reaction scheme (where Ar=an ortho-nitro substituted aromatic ring):

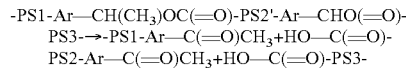

Thus, a fragment containing polymeric segment PS2 is generated which is no longer covalently bound to the remainder of the hydrogel structure.

FIG. 1 shows, in schematic form, an illustrative, exemplary embodiment of the present invention wherein a hydrogel network capable of undergoing degradation via multiple modes is formed in Part A by reaction of Polymer A and Polymer B. Polymer A is a maleimide-functionalized macromer based on a four-arm polymer (which could be a four-arm polyethylene glycol, for example) that contains photodegradable moieties (in this case, ortho-nitro benzyl moieties wherein the carbon attached to the benzene ring is substituted with an ester group, the ester group being capable of being cleaved when exposed to light, as illustrated in Part C). Two or more of the four arms of Polymer A are similarly functionalized with both a maleimide group and a photodegradable moiety (for simplicity, Polymer A is drawn in FIG. 1 to show only one functionalized terminus). Polymer B is an arylthiol-functionalized macromer based on a four-arm polymer (which could be a four-arm polyethylene glycol, for example). Polymer B contains ester moieties, which are capable of undergoing hydrolytic degradation once Polymer B has been incorporated into the hydrogel network (see Part E of FIG. 1).

Polymer A and Polymer B react with each other as illustrated in Part B of FIG. 1, typically under relatively mild conditions, to form the crosslinked hydrogel network. For example, the reaction may be carried out at a temperature of from about 20° C. to about 40° C. in an aqueous environment, i.e., in the presence of water; typically, no catalyst is needed. The thiol functional groups present in Polymer A react with the maleimide functional groups of Polymer B in a Michael-type addition reaction, to form thioether linkages. These thioether linkages are capable of participating in retro Michael-type addition and thiol exchange reactions, such as an exchange with glutathione (GSH), as illustrated in Part D of FIG. 1. Each junction between a Polymer A and a Polymer B in the schematic of the ideal hydrogel network shown in Part A of FIG. 1 contains a thioether moiety (capable of degradation via a thiol exchange reaction, as shown in Part D), a photodegradable moiety (which is capable of being cleaved upon exposure to light, for example, as shown in Part C), and an ester moiety (which is capable of being hydrolyzed, as shown in Part E). The thioether moiety, the photodegradable moiety and the ester moiety are each in the backbone of the hydrogel network. The hydrogel network is capable of undergoing degradation involving scission of the linkages by different modes (thereby, for example, releasing one or more cargo substances that may have been initially encapsulated within the hydrogel network, in response to conditions present in the environment surrounding the hydrogel or applied externally and on demand).

Exemplary Starting Materials and Illustrative Methods of Making Hydrogels

Hydrogels in accordance with the present invention may be prepared through the use of "click" reactions between multifunctional starting materials wherein one or more of the starting materials is functionalized with multiple thiol groups and one or more of the starting materials is functionalized with multiple α,β-unsaturated carbonyl groups, such as maleimide groups or other groups containing two carbonyl groups in conjugation with a carbon-carbon double bond (e.g., —C(═O)CH═CH—C(═O)—). The functional groups on the starting materials may be terminal functional groups (i.e., positioned at the terminus of a molecule) and/or pendant to the backbone of the starting material. The thiol and α,β-unsaturated carbonyl groups are capable of reacting rapidly through a Michael-type addition reaction to form thioether linkages (which are thioether succinimide linkages, in the embodiment where the α,β-unsaturated carbonyl group is a maleimide group), which serve to link together polymeric segments in the hydrogel. At least one of the starting materials is a macromer (macromonomer), which functions to introduce polymeric segments into the resulting hydrogel. In one embodiment, all of the starting materials are macromers. As used herein, a "macromer" is a molecule comprising two or more repeating units and reactive functional groups (e.g., reactive functional end groups) that allow reaction with another functional group. However, it is also possible to employ functionalized starting materials which are not macromers, provided that at least one of the starting materials is a macromer with m functional groups, where m is an integer of two or more. For example, one of the starting materials may be a non-macromeric compound corresponding to the generic structure $R(Z)_n$, wherein R is an n valent monomeric organic moiety, Z is a thiol functional group or an α,β-unsaturated carbonyl group, and n is an integer of two or more (or three or more, where the other starting material containing functional groups reactive with the functional groups Z of the generic structure $R(Z)_n$ bears only two such reactive functional groups).

At least one of the starting materials must contain at least three reactive functional groups per molecule, in order to achieve a crosslinked network structure in the resulting hydrogel. In one embodiment of the invention, all of the starting materials contain at least three reactive functional groups per molecule.

Figure 3:
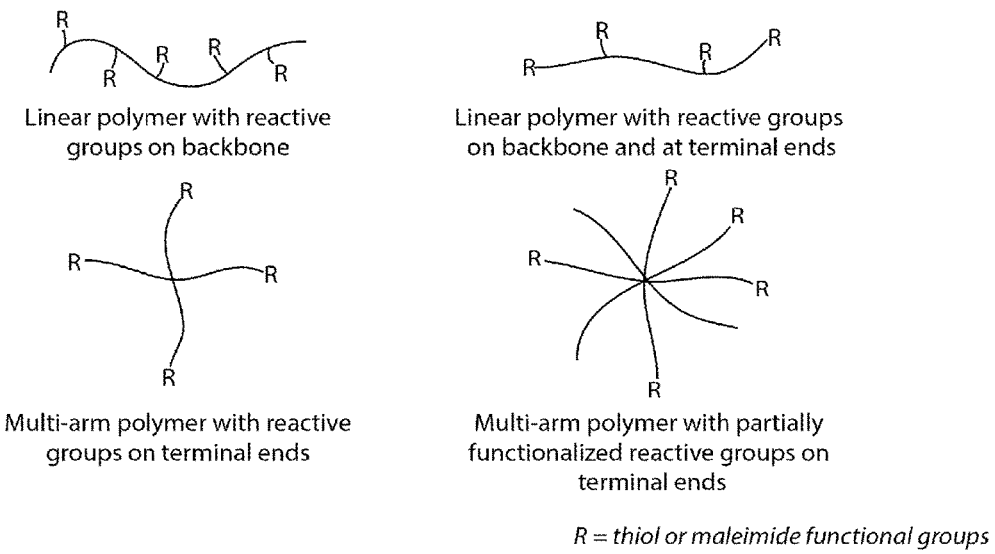
FIG. 3 shows, in schematic form, various illustrative types of functionalized polymers (macromers) which may be utilized to prepare hydrogels in accordance with the invention as well as specific, illustrative examples of the types of functional groups that may be present in such macromers.
Figure 3:
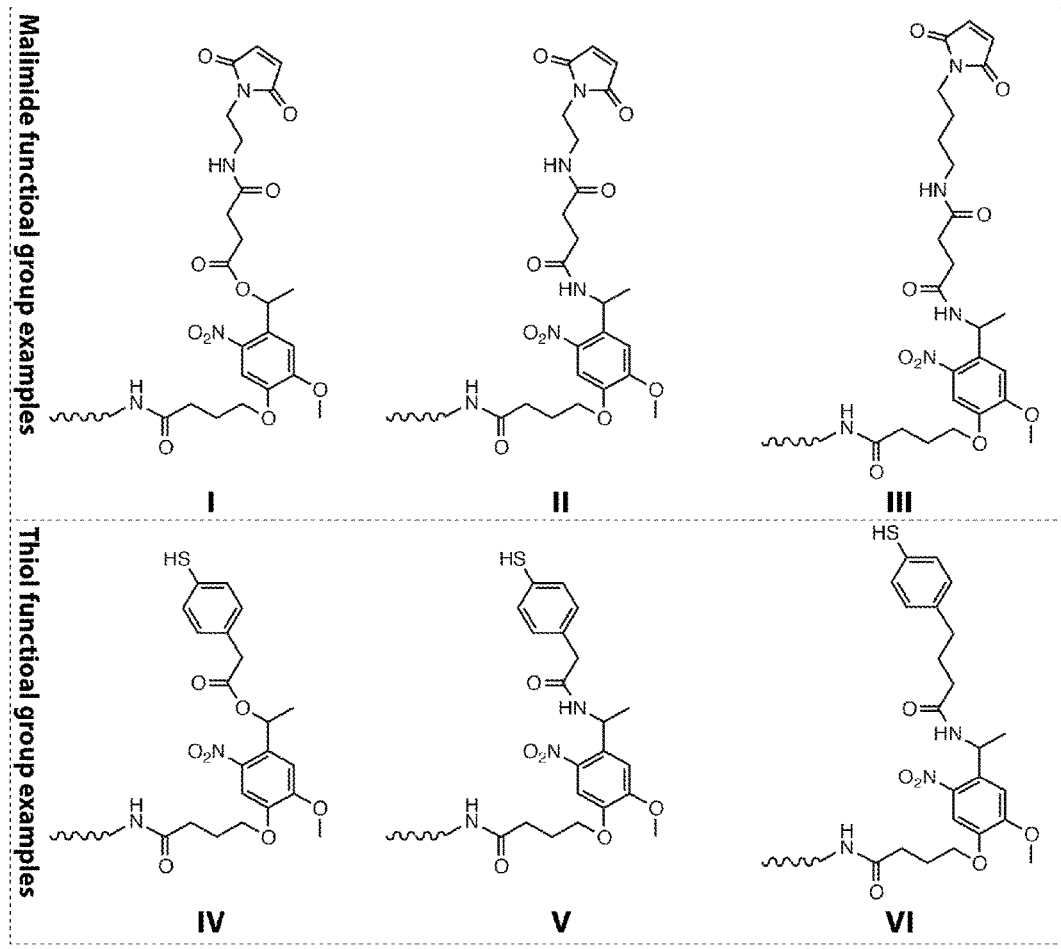

The upper portion of FIG. 3 illustrates in schematic form certain of the types of functionalized polymers which may be used to prepare hydrogels in accordance with the present invention. The functionalized polymer may be linear or multi-arm and may bear functional groups pendant on its backbone, at terminal ends or both pendant on its backbone and at one or more of its terminal ends. One or more of the terminal ends of the polymer may be functionalized; in one embodiment, all of the terminal ends of the polymer are functionalized.

A photodegradable moiety may be located proximate to a thiol or α,β-unsaturated carbonyl group in the functionalized polymer. Specific illustrative examples of maleimide and thiol functional groups proximate to photodegradable groups (e.g., an ortho-nitro benzyl ester or amide moiety) are shown in the lower portion of FIG. 3.

A method of making a hydrogel is additionally provided by the present invention, wherein the method comprises reacting a functionalized polymer bearing at least x functional groups X with a functionalized linker molecule bearing at least y functional groups Y, wherein a) x and y are each independently an integer of 2 or more and x+y is an integer of 5 or more; b) X and Y are different from each other and are selected from the group consisting of α,β-unsaturated carbonyl and thiol; c) at least one of the functionalized polymer or the functionalized linker molecule has a backbone containing at least one photodegradable moiety; and d) X and Y react to form a thioether linkage. In one embodiment of the invention, X and Y are selected from the group consisting of maleimide and arylthiol (e.g., X may be maleimide and Y may be arylthiol or X may be arylthiol and Y may be maleimide). The functionalized polymer may be a functionalized polyether, functionalized polypeptide or functionalized polysaccharide, for example. The functionalized linker molecule, in one embodiment of the invention, may be a polyether, polypeptide or polysaccharide bearing at least y functional groups Y.

The at least one photodegradable moiety may include at least one photodegradable moiety containing an ester or amide linkage that undergoes irreversible cleavage upon being irradiated with UV, visible or IR light. For example, the photodegradable moiety may include at least one photodegradable moiety selected from the group consisting of nitro-substituted benzyl ester moieties. One type of photodegradable moiety useful in the present invention contains a nitro group ortho to an ester or amide functionality on an aromatic ring structure. For example, the photodegradable moiety may include at least one photodegradable moiety having the general structure —Ar(NO₂)—CHR'—Z—C(=O)—, wherein Ar is an aromatic moiety (such as a benzene ring) substituted with a nitro group ortho to —CHR'—, Z is O or NH, and R' is H or alkyl (e.g., R'=C1-C6 alkyl, such as methyl). In one embodiment of the invention, the aromatic moiety is additionally substituted with an ether group (e.g., methoxy, ethoxy) meta to —CHR'—. Ether substitution at the meta position of the aromatic moiety is useful for the purpose of increasing the sensitivity of the photodegradable moiety to longer wavelengths of light (e.g., long wavelength UV or visible light).

Another type of photodegradable moiety useful in the present invention is a coumarin moiety in which an ester or amide group is substituted on a methylene carbon attached to the 4 position of a coumarin structure. For example, the photodegradable moiety may include at least photodegradable moiety having the general structure —CM-CHR'—Z—C(=O)—, wherein CM is a coumarin moiety, the group —CHR'— is substituted at the 4 position of the coumarin moiety, Z is O or NH, and R' is H or alkyl (e.g., C1-C6 alkyl, such as methyl).

In one embodiment of the invention, X and Y are selected from the group consisting of maleimide and arylthiol (e.g., X may be maleimide and Y may be arylthiol or X may be arylthiol and Y may be maleimide).

In one embodiment of the invention, the functionalized polyether or the functionalized linker molecule corresponds to structure (I):

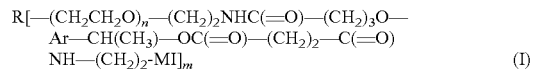

wherein R is an organic moiety, n is an integer of 2 or more (e.g., 2 to 200), Ar is a nitro-substituted aromatic ring, R' is H or alkyl (e.g., C1-C6 alkyl, such as methyl), MI is a maleimide moiety having a nitrogen atom covalently bonded to —(CH₂)₂— and m is an integer of 2 or more (e.g., 2, 3, 4, 5, 6, etc.).

In another embodiment of the invention, the functionalized polymer or the functionalized linker molecule corresponds to structure (IV):

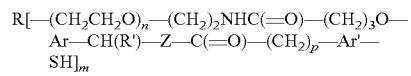

(IV), wherein R is an organic moiety, n is an integer of 2 or more (e.g., 2 to 200), Ar is a nitro-substituted aromatic ring, R' is H or alkyl (e.g., C1-C6 alkyl, such as methyl), Z is O or NH, Ar' is an aromatic ring, p is an integer of 1 or more (e.g., 1, 2, 3, 4, etc.), and m is an integer of 2 or more (e.g., 2, 3, 4, 5, 6, etc.).

Methods of functionalizing polymers such as polyethers (e.g., polyethylene glycols) to provide macromers containing thiol functional groups (either arylthiol or aliphatic thiol groups) or α,β-unsaturated carbonyl functional groups capable of reacting with thiols in Michael-type addition reactions (such as maleimide groups, for example) are well known in the art. See, for example, US Pat. Pub. No. 2013/0244975 and Baldwin et al., Polymer Chemistry, Vol. 4(1), 133-143 (2013), the entire disclosure of each of which is incorporated herein by reference in its entirety for all purposes. Such chemistries can be readily adapted for use in the present invention. The particular thiol and α,β-unsaturated carbonyl functional groups present in the functionalized polymer and functionalized linker molecules used as precursors to prepare hydrogels in accordance with the present invention are preferably selected such that reaction between the two types of groups takes place relatively rapidly at around room or human body temperature (e.g., about 20° C. to about 40° C.), without any catalyst being present. The Michael-type addition reaction which occurs between the functional groups leads to covalent linkages (thioether bonds) between the functionalized polymer and the functionalized linker molecule, resulting in the desired three dimensional network structure of a hydrogel. At least one of the functionalized polymer or functionalized linker molecule contains more than two functional groups per molecule, thus ensuring that the polymeric reaction product thereby obtained is desirably cross-linked rather than linear. Increasing the number of functional groups per molecule will typically result in a higher crosslink density. The spacing between the multiple reactive functional groups on the functionalized polymer and the functionalized linker molecule will influence the size of the openings in the network of the hydrogel formed. For example, if a terminally-functionalized multi-arm polyether is employed as a reactant, a polyether having longer (higher molecular weight) arms will provide (assuming the other reactant used is not changed) a hydrogel having larger network openings (i.e., a greater mesh size) as compared to an analogous functionalized polyether having shorter (lower molecular weight) arms.

Figure 2:
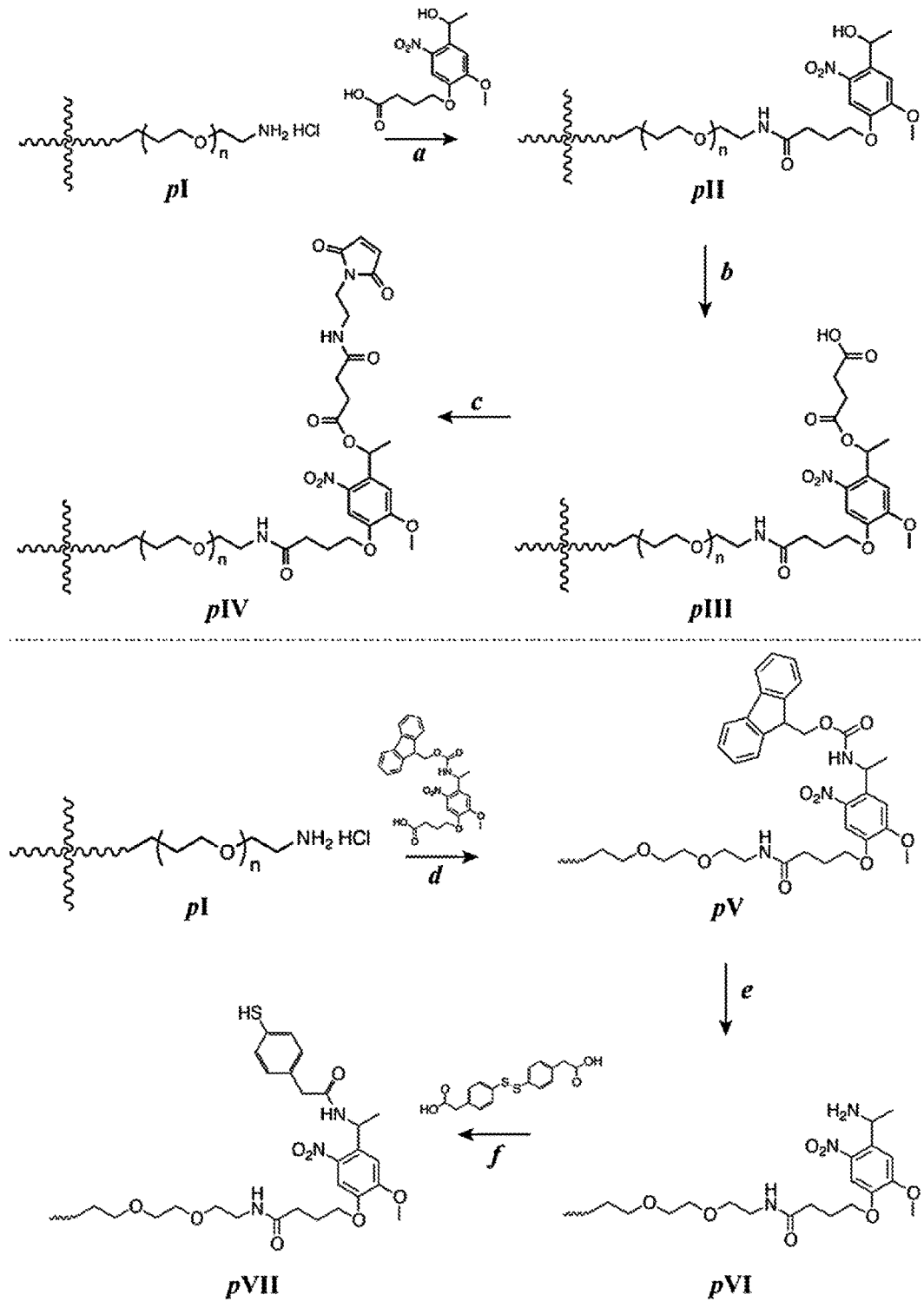
FIG. 2 shows synthetic schemes by which maleimide-functionalized and thiol-functionalized macromers containing photodegradable moieties useful as starting materials for hydrogels can be prepared.

The upper portion of FIG. 2 shows, in schematic form, an exemplary synthesis route which may be used to prepare a macromolecular crosslinker functionalized with photodegradable maleimide suitable for use as a starting material in the preparation of hydrogels in accordance with the present invention. This reaction scheme generally illustrates the procedure hereafter described in the Examples for synthesizing PEG-4-PD-MI, which is a polyethylene glycol having four arms wherein the terminus of each of the four arms contains a photodegradable moiety based on an ortho-nitro benzyl moiety as well as a maleimide functional group capable of reacting with an α,β-unsaturated carbonyl group. For simplicity, FIG. 2 only shows the chemical transformations occurring at one terminus of the multi-arm polyether. The four-arm polyethylene glycol provides polyoxyethylene-containing polymeric segments to a hydrogel network, once the terminal maleimide groups have been reacted with a polythiol-functionalized starting material.

In step a of the synthetic scheme shown in the upper part of FIG. 2, a four-arm polyethylene glycol having primary amine end groups (PEG-4-NH$_2$, pI) is reacted with 4-(4-(1-hydroxyethyl)-2-methoxy-5-nitrophenoxy) butanoic acid (prepared using the procedure described in Kloxin et al., Nat Protoc 2010, 5, 1867) to yield hydroxyl-functionalized intermediate pII.

Intermediate pII is then reacted with succinic anhydride in step b to produce carboxylic acid-functionalized intermediate pIII, which in turn is reacted with succinic anhydride in step c to produce the desired product pIV (PEG-4-PD-MI). PEG-4-PD-MI is a four-arm polyethylene glycol containing both a photodegradable moiety and a reactive maleimide functionality at the end of each of its four arms.

The reagents and conditions used in these steps may be summarized as follows:
Step a: DIPEA, HATU in DMF under Ar;
Step b: Succinic anhydride, DMAP in DMF under Ar at 50° C.;
Step c: N-(2-aminoethyl)maleimide, TFA, DIPEA, HATU in DMF under Ar.

In addition, FIG. 2 (lower part) shows the synthesis of PEG-4-PD-SH (a four-arm polyethylene glycol containing both a photogradable moiety and a reactive thiol functionality at the end of each of its four arms). In step d of the synthesis scheme shown in the lower part of FIG. 2, a four-arm polyethylene glycol having primary amine end groups (PEG-4-NH$_2$, pI) is reacted with 4-(4-(1-((((9H-fluoren-9-yl)methoxy)methyl)amino)ethyl)-2-methoxy-5-nitrophenoxy)butanoic acid to yield Fmoc-protected amine-functionalized intermediate pV.

Intermediate pV is then reacted with piperidine (20% in DMF) in step d to produce amine-functionalized intermediate pVI, which in turn is reacted with 2,2'-(disulfanediylbis (4,1-phenylene))diacetic acid and subsequently reduced using tris(2-carboxyethyl)phosphine in step f to produce the desired product pVII (PEG-4-PD-SH).

The reagents and conditions used in these steps may be summarized as follows:
Step d: DIPEA, HATU in DMF under Ar;
Step e: 20% piperidine in DMF at room temperature;
Step f: 2,2'-(disulfanediylbis(4,1-phenylene))diacetic acid, DIPEA, HATU in DMF under Ar followed by tris(2-carboxyethyl)phosphine in water at room temperature.

The above-described methods (i.e., reaction of thiol- and α,β-unsaturated carbonyl-functionalized starting materials) may be carried out in the presence of one or more cargo substances, which will result in cargo substance(s) being entrapped within the three dimensional network of the hydrogel as it forms. Cargo substances may also be incorporated pendant to the backbone of the hydrogel network, for example by the formation of degradable or non-degradable linkages between the cargo substance and the hydrogel backbone. Such procedures will yield compositions useful for the controlled delivery of the cargo substance(s).

Cargo Substances

The hydrogels of the present invention are useful for the encapsulation of cargo substances, wherein a cargo substance (or multiple cargo substances) may be initially trapped within the three-dimensional network of the linked polymeric segments of a hydrogel, with the cargo substance(s) thereafter being released through degradation of the hydrogel. In other embodiments, cargo substances can be immobilized via non-covalent and/or covalent bonds to the hydrogel network. A covalent linkage between a cargo substance and the hydrogel network may, for example, contain one or more degradable linkages of the type described herein, such as a photodegradable linkage, a thioether linkage capable of undergoing a retro Michael-type addition reaction and thiol exchange, and/or a hydrolysable linkage.

The types of substances which may be utilized as cargo substances in the present invention are not particularly limited, but generally are relatively small in size. Typically, suitable cargo substances are, in various embodiments of the invention, not greater than 500 microns, not greater than 100 microns, not greater than 10 microns, not greater than 1 micron, not greater than 100 nm, or not greater than 10 nm in their longest dimension. Nanoparticles as well as microparticles may thus be employed as cargo substances. The cargo substance may be organic, inorganic or a hybrid thereof (i.e., a hybrid organic/inorganic substance). In various embodiments of the invention, the cargo substance may be a bioactive substance (that is, a substance having biological activity) or a bioinactive substance. The cargo substance may also be a substance containing both a bioactive component and a bioinactive component (such as, for example, a bioactive supported on a biologically inactive carrier). The cargo substance may also be a pro-drug.

In one embodiment, the cargo substance is not covalently bound to the hydrogel, but rather is physically entrapped within the three dimensional network of the hydrogel (wherein its dimensions do not permit it to fit through the openings of the network, until such time as at least partial degradation of the hydrogel takes place leading to enlargement of the network openings). In another embodiment, however, the cargo substance is bound to the hydrogel, such as through a covalent or ionic bond or complexation. In the embodiment where the cargo substance is covalently bound to the hydrogel, the covalent bonding or link between the cargo substance and the hydrogel may contain at least one degradable moiety, such as a photodegradable moiety, a thioether capable of undergoing a thiol exchange reaction or a hydrolyzable moiety, that degrades (cleaves) upon exposure to certain stimuli or conditions (light irradiation, or exposure to a reducing or hydrolytic environment, for example), thereby freeing the cargo substance.

The cargo substance may be a small molecule, such as a drug. In other embodiments, the cargo substance may be a natural or synthetic substance or a natural substance that has been synthetically modified or derivatized in some manner. Polymeric substances, both natural and synthetic, may be employed as suitable cargo substances, as can cells and the like.

Illustrative examples of substances that may be utilized as cargo substances in accordance with the present invention include, but are limited to, the following: small molecule drugs, biomolecules, biomacromolecules (including, but not limited to, polysaccharides, glycosaminoglycans, and proteins), cells (including live cells), therapeutic agents (i.e., agents that cause a measurable physiological response in an animal, such as a human), fluorophores, chromagenic agents, enzymes, proteins (including immunomodulatory proteins and matrix metalloproteinases), antibiotics, anesthetics, antibodies, growth factors, hormones, anti-inflammatories, analgesics, cardiac agents, psychotropics, fillers (e.g., inorganic and/or polymeric particles), immunotherapeutics, cytokines, oligonucleotides, labels (e.g., fluorophores, radionucleotides, fluorescent moieties, chemiluminescent moieties, magnetic particles, dyes) and the like and combinations thereof.

Illustrative End Uses

The present invention involves the use of a responsive hydrogel-based material as a carrier system capable of in situ delivery of various bioactive and/or bioinactive moieties, including small molecules, biomolecules, biomacromolecules and cells. The above-described hydrogels enable finely tuned local release of cargo molecules and material constituents as a function of the in vivo tissue environment (e.g., enzyme concentration or reducing environment) and/or externally applied stimuli (e.g., light) by selective spatiotemporal hydrogel degradation. The hydrogels of the present invention permit local, controlled therapeutic release of bioactive substances for increased efficacy with reduced side effects, as compared to other methods of administering such bioactive substances.

The compositions of the present invention which comprise a hydrogel and a cargo substance encapsulated and/or bound therein permit the design of controlled drug delivery systems in which a drug is delivered to a target organ or site in a controlled manner by means of light exposure, a reducing environment and/or hydrolysis in the presence of water. More specifically, the hydrogel-based system can be used to deliver various chemotherapies (e.g., small molecules) and/or immunotherapies (e.g., antibodies and other proteins) to target organs, such as an epidermal site for skin cancer. The reducing environment in carcinoma tissues, externally applied light and/or ester hydrolysis (depending upon the types of degradable linkages present in the hydrogel) will essentially drive the release of chemotherapeutics or immunotherapeutics. The former two modes of degradation will provide greater control over the release of cargo molecules by varying the nucleophilicity of the thiol used to create a thioether linkage by reaction of the thiol with an $\alpha,\beta$-unsaturated carbonyl functionality and by varying the extent (duration) and intensity of externally applied light.

In another embodiment of the invention, a bioactive coating and delivery system is provided, in which a thin layer of hydrogel containing bioactive molecules is applied on an implant surface or as a wound dressing and the release of the bioactive molecules (such as Insulin-like Growth Factors (IGFs) or Bone Morphogenetic Proteins (BMPs)) can be finely controlled by incorporation of different types of degradable linkages in the hydrogel structure. For example, a retro Michael-type addition and thiol exchange reaction (leading to scission of a thioether linkage), external light (resulting in cleavage of a photodegradable linkage) and/or hydrolysis of an ester or amide linkage can provide release of the bioactive molecules.

A further embodiment of the invention provides a cell delivery system, wherein a hydrogel is used as a carrier to deliver cells as therapeutics to acutely injured or chronically diseased tissue for regenerative medicine purposes. The incorporation of multi-mode degradable chemistries in the hydrogel will provide preprogrammed and/or sequential release of cells encapsulated in the hydrogel, as per user requirements.

A composition in accordance with the present invention, comprising a hydrogel (or combination of hydrogels) which encapsulates a cargo substance (or combination of cargo substances) and/or which has a cargo substance (or combination of cargo substances) attached thereto (covalently or non-covalently) may be administered to a subject using any suitable technique. The composition may further comprise a physiologically acceptable carrier or diluent, such as water or a buffer. Suitable carriers, diluent and other excipients (e.g., lyophilization agents such as saccharides) are well known in the art. The amount of cargo substance(s) administered to the subject may be varied and selected as may be needed or desired in order to provide the desired effect. For example, where the subject has a medical condition and the cargo substance is a bioactive substance having activity in treatment of that medical condition, the administered amount of a composition in accordance with the present invention is tailored to provide a dosage of the bioactive substance effective to treat the medical condition. By adjusting the degradation characteristics of the hydrogel, as described herein, the release profile of the bioactive substance may be modified so as to optimize or improve the response of the subject to the bioactive substance.

The composition may be administered to the subject over a period of hours, days, weeks or months. It may also be administered a single time, or once, twice, thrice or more times a day, once every two days, once every three days, once every four days, once every five days, once every six days, once a week, once every 10 days, once every two weeks, once every three weeks, once a month, or even less frequently.

The composition may be formulated, for example, for oral, sublingual, intranasal, intraocular, rectal, transdermal, mucosal, topical or parenteral administration. Parenteral administration may include intradermal, subcutaneous (s.c., s.q., sub-Q, Hypo), intra-articular (i.a.), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids) administration. Any device suitable for parenteral injection or infusion of the composition may be used for such administration. In one embodiment, the composition is injectable and is administered by injection. In another embodiment, the composition is applied topically. In yet a further embodiment, the composition is administered by implantation.

The hydrogels and compositions of the present invention are useful for the following exemplary purposes, among others: therapeutics (e.g., delivery of drugs, proteins, cells, microparticles and nanoparticles); wound healing patches; tissue engineering scaffolds; barriers for tissue injury healing; cell encapsulation platforms; and implant coatings.

In one embodiment, the hydrogel (e.g., a hydrogel containing one or more cargo substances encapsulated therein) is preformed and then administered to a subject. Alternatively, the hydrogel may be formed in situ, by administering hydrogel precursors, together with one or more cargo substances, which then react to form the hydrogel encapsulating the cargo substances. In another embodiment, the hydrogel is formed in situ by administering hydrogel precursors to a subject, by injection for example, wherein at least one of the hydrogel precursors contains, as part of its structure, a bioactive moiety that is capable of being liberated from the hydrogel upon degradation of the hydrogel through one or more degradation modes such as photo-initiated cleavage (of an ester group adjacent to an ortho-nitro substituted aromatic ring, for example), a thiol exchange reaction (leading to cleavage of a thioether linkage) and/or hydrolysis (of ester and/or amide linkages, for example). The covalently bonded bioactive moiety may be in the backbone of the hydrogel network or pendant to a polymeric segment of the hydrogel network.

Following administration of the hydrogel-containing or formation of the hydrogel-containing composition in situ, the cargo substance(s) may thereafter be released from the hydrogel by one or more suitable stimuli, which may be endogenous (e.g., water, enzymes, reducing microenvironments) and/or exogenous (e.g., light).

EXAMPLES

Design and Synthesis of Building Blocks with Different Degradable Functional Groups Several multiarm poly(ethylene glycol) (PEG)-based macromers with different reactive functionalities were created for the rational design of biocompatible, responsive hydrogels with distinct levels for controlled degradation, from preprogrammed and responsive to externally tunable. Specifically, four-arm polyethylene glycol (PEG) end-functionalized with thiols (PEG-4-SH) was reacted with four-armed photodegradable PEG end-functionalized with maleimides (PEG-4-PD-MI) by a Michael-type addition reaction (FIG. 1, Part A). PEG, a hydrophilic polymer FDA-approved for various applications, is facilely modified with appropriate reactive functional groups for tailoring of the hydrogel properties while limiting any non-specific protein-material interaction. Exemplary degradable functional units for the photodegradable and reducing environment sensitive macromers are ortho-nitro benzyl (o-NB) and mercaptophenylacetic acid (MPA)-based succinimide thioether linkages, respectively. Upon the application of cytocompatible doses of light, the photolabile o-nitrobenzylether linkage undergoes irreversible cleavage due to photochemically induced photoisomerization yielding ketone and carboxylic acid-based cleavage products (FIG. 1, Part C).

PEG-4-SH was synthesized via esterification by reacting mercaptophenylacetic acid with the hydroxyl end groups of four-armed PEG (following the procedures described in US Pat. Pub. No. 2013/0244975). Aryl-thiol based succinimide thioether linkages undergo retro Michael-type addition and thiol exchange in the presence of glutathione (GSH), which provides a reducing microenvironment (FIG. 1, Part D). Since the concentration of glutathione is elevated in carcinoma tissues compared to surrounding healthy tissues, the incorporation of aryl-thiol-based linkages that cleave in response to glutathione can allow higher release of therapeutics in carcinoma tissues providing higher therapeutic efficacy. In addition, both macromers (PEG-4-PD-MI and PEG-4-SH) contain an ester linkage, allowing for hydrolysis of the resulting polymeric network under aqueous conditions, eventually leading to complete degradation of the hydrogel in aqueous environments. Overall, the incorporation of multiple cleavable groups that can degrade in response to endogenous and exogenous stimuli presents an attractive strategy for designing drug delivery systems with complex release profiles that can be tuned for the needs of an individual patient.

A suitable method that can be used for synthesis of the PEG-4-PD-MI macromer involves modifying the end groups of PEG by sequential reactions to build on the photodegradable maleimide group. A small precursor of the photolabile group is synthesized and coupled with the amine end groups of PEG. The PEG-photolabile precursor is subsequently modified with maleimide end groups to create a PEG crosslinker end-functionalized with photodegradable maleimide (FIG. 2). To achieve this, an intermediate, 4-(4-(1-hydroxyethyl)-2-methoxy-5-nitrophenoxy) butanoic acid (FIG. 2), was first synthesized using a protocol published by Kloxin et al., Nat Protoc 2010, 5, 1867. The carboxylic groups from the intermediate were activated with HATU in the presence of organic base (DIPEA) to form an amide linkage with four-arm PEG amine (PEG-4-$NH_2$, pI in FIG. 2). This reaction yielded a polymer-photolabile precursor intermediate with hydroxyl end groups (pII in FIG. 2) with 99% conversion as assessed using aromatic proton area integration in $^1$H NMR spectra. Multiarm PEG (four-arm) maleimide was employed instead of linear PEG to provide an additional degree of functionalization and subsequent control over mechanical properties. The hydroxyl groups from pII were subsequently reacted with succinic anhydride to convert the end groups to carboxylic acid end groups, producing an acid-functionalized photodegradable polymer intermediate (pIII). The reaction yield was ~79%, and the functionality (~100%) was quantified from the disappearance of the hydroxyl proton at 5.26 ppm on the $^1$H NMR spectra. The carboxylic acid groups were activated using HATU to form an O-acyl(tetramethyl)-active ester that can react with the nucleophilic amine end of N-(2-aminoethyl) maleimide (AEM). This reaction yielded maleimide-functionalized photodegradable 4-arm PEG (pIV, PEG-4-PD-MI) with a reaction yield of 82% and functionality of 79%, as quantified using the maleimide ring protons on $^1$H NMR spectra. The lower functionalization with maleimide observed here, as compared to the other end group modification reactions, may be attributed to two side reactions: free amines of AEM may react with maleimides on other AEM molecules, and the maleimide ring may undergo hydrolysis during the purification and cleanup processes.

Hydrogel Formation and Tunable Mechanical Properties

The mechanical properties of hydrogels formed using the synthesized multifunctional macromolecular monomers were first investigated to establish a range appropriate for various biomedical applications. In particular, hydrogel gelation kinetics and mechanical properties play a crucial role in the clinical transition of the injectable multimode degradable hydrogels for controlled drug delivery applications. Here, dynamic time sweep rheological experiments were conducted to monitor the gelation kinetics and to demonstrate the utility of these functionalized macromolecules to form crosslinked networks on timescale appropriate for injection. Hydrogels were formed in situ (i.e., on the rheometer stage) by mixing precursor solutions of photodegradable PEG-4-PD-MI and reducing-microenvironment sensitive PEG-4-SH at a 1:1 ratio of maleimide to thiol. The mixed precursor solution was added to the rheometer stage before any apparent increase in the solution viscosity, and time sweep measurements were acquired under the viscoelastic regime. Due to rapid gelation kinetics, the crossover point of storage and loss moduli, which is an indirect measurement of the gel point, occurred prior to the first measurement on the rheometer. The consistent increase in storage modulus (G') without a significant increase in loss modulus (G") as a function of time which was observed highlights the elastic nature of the hydrogels. Properties that are critical for the success of injectable hydrogel-based drug carriers, especially mesh size that dictates the diffusion of solutes in and out of the hydrogel, are dependent on the mechanical properties of hydrogels and vary with the network crosslink density. The impact of crosslink density on the hydrogel elastic properties was investigated by varying the polymer concentration. With an increase in the total polymer concentration from 2 to 5 wt %, the storage modulus increased from 0.2 kPa to 3.7 kPa, where this order of magnitude range of moduli matches well with that of various soft tissues (from that of brain to muscle, G~E/3). The corresponding mesh size, calculated by Flory-Rehner, varied between 10 nm to 14 nm as a function of polymer concentration, providing a means to control entrapment and diffusion of cargo molecules for achieving desired release profiles. The crosslinking time, defined here as the time to reach 90% of the final storage modulus value, ranged from approximately 2 to 10 minutes. The gelation kinetics and elastic properties of these novel PEG hydrogels are consistent with the gelation kinetics of similar Michael-type crosslinked PEG hydrogels. Overall, these results indicate that the gelation time and initial elastic properties of these multimode degradable hydrogels formed using Michael-type addition reactions can be tuned over relevant ranges for several applications, including injectable drug delivery vehicles and in vitro responsive cell culture platforms.

Degradation in Response to Exogenous and Endogenous Stimuli

A range of degradation profiles and times that could be achieved with these multifunctional gels in detailed studies of their degradation kinetics in response to light, reducing microenvironment, and aqueous microenvironment was next established. Changes in the elastic properties of the hydrogels were monitored as a function of time upon application of each stimulus, focusing on the 5 wt % composition whose mesh size is appropriate for release of large cargo substances (e.g., antibodies, nanoparticles, and cells). To study the light-mediated degradation of the multimode degradable hydrogels, samples formed in situ on a photorheometer were irritated with cytocompatible doses of light (10 mW/cm$^2$ at 365 nm [long wavelength UV] or 400-500 nm [visible]). The elastic properties during degradation were monitored using time sweep measurements. The hydrogel shear modulus is directly correlated with the crosslink density per the theory of rubber elasticity (G~ρx), and a decrease in the storage modulus thus indicates cleavage of crosslinks and degradation of the hydrogel. The degradation behavior of multimode degradable hydrogels was compared with a negative control (gels formed using PEG-4-SH and PEG-4-MI which do not contain photodegradable moieties). A significant decrease in storage modulus for the multimode degradable hydrogel was observed with the application of short pulses of light (30-second of 365 nm), whereas the elastic properties of control hydrogel remained unchanged. These data confirm triggered degradation of multimode degradable hydrogels in response to light. The rate of degradation in response to applied light was calculated using continuous degradation data assuming first order degradation kinetics based on network connectivity and kinetics of photocleavage. The rate constant (k) for the initial degradation time period was found to be 0.304 min$^{-1}$±0.014 min$^{-1}$ ($t_{1/2}$=2.28 min) and compares well with typical rate constants for cleavage of similar o-nitrobenzyl ether based moieties (k~0.2-0.3 min$^{-1}$). The ability to control degradation using externally applied light provides opportunities to control the drug release in real time for each patient's need in controlled drug delivery as well as to control the network properties for hydrogel based in vitro cell culture applications.

Arylthiol-functionalized PEG macromers provide degradability in response to reducing microenvironments within the multimode degradable hydrogels. Glutathione (GSH) is a reducing agent produced at increased levels by highly metabolically active cells, and consequently, is found at elevated concentrations in carcinoma tissues. Chemistries that respond to reducing conditions such as this provide an opportunity for controlled release of therapeutics in rapidly developing tissues such as tumors. To study hydrogel degradation in response to a GSH-rich microenvironment, multimode degradable hydrogels were suspended in buffer with a physiologically-relevant concentration of GSH (10 mM), and the elastic properties of the hydrogels were monitored periodically using oscillatory rheometery. Nondegradable PEG hydrogels without photolabile or reducing environment sensitive linkages (PEG-4-MI and PEG-4-SH with alkyl thiols) and similar mechanical properties were used as a negative control. Both control and multimode degradable hydrogels show initial decrease in storage modulus, which can be attributed to initial equilibrium swelling of the hydrogels. Notably, a continuous decrease in modulus for multimode degradable gels is observed after initial swelling, confirming degradation of these hydrogels in response to the reducing microenvironment. Side reactions, such as maleimide ring hydrolysis that results in a non-degradable crosslink, also can impact the rate and extent of gel degradation; however, the thiol exchange reaction occurs orders of magnitude faster than this side reaction. Further, ester hydrolysis provides a third mechanism for degradation, but its rate also is significantly slower than the thiol exchange reaction. Degradation of the multimode hydrogels in reducing environments without applied light consequently should be dominated by the thiol exchange reaction. The observed kinetics for early degradation were pseudo-first-order with a rate constant of 1.52×10$^{-3}$ min$^{-1}$±3.06×10$^{-6}$ min$^{-1}$ ($t_{1/2}$=450 min), which is consistent with earlier reported values for similar hydrogels. Complete hydrogel dissolution (i.e., reverse gelation) was observed after approximately 2 days (at 2880 minutes), which is faster than observed in earlier studies of dually degradable hydrogels that did not contain a photolabile group (complete dissolution at ~4 days). Without wishing to be bound by theory, it is believed that this disparity is due to the elevated rate of hydrolysis of esters present in the PEG-4-PD-MI, since an earlier study indicated that the ester linkage present on the PEG-4-SH is relatively stable with a half-life of 14 days. To test this hypothesis and further characterize multimode hydrogel degradation, hydrolytic cleavage studies were conducted, characterizing the degradation of multimode hydrogels over time in an aqueous solution without GSH. The rate of ester hydrolysis was found to be $6.84 \times 10^{-4}$ min$^{-1} \pm 9.19 \times 10^{-6}$ min$^{-1}$ ($t_{1/2}$=1013 min, pseudo-first order kinetics), which was an order of magnitude larger than observed dually degradable hydrogels without the photolabile group in previously reported studies (k=$1.89 \times 10^{-5}$ min$^{-1}$).

Thus, the degradation of multimode hydrogels can be controlled over minutes to days, with half-lives ranging from ~2 minutes to ~1000 minutes based on a kinetics analysis. This range of timescales achieved with externally triggered, reducing responsive, and pre-programmed cleavage is attractive for drug delivery and tissue engineering applications, as well as for in vitro cell culture platforms where dynamic changes in materials are useful for studying and assaying cell-material interactions.

Degradation Mediated Release of Model Cargo Nanobeads

Figure 4:
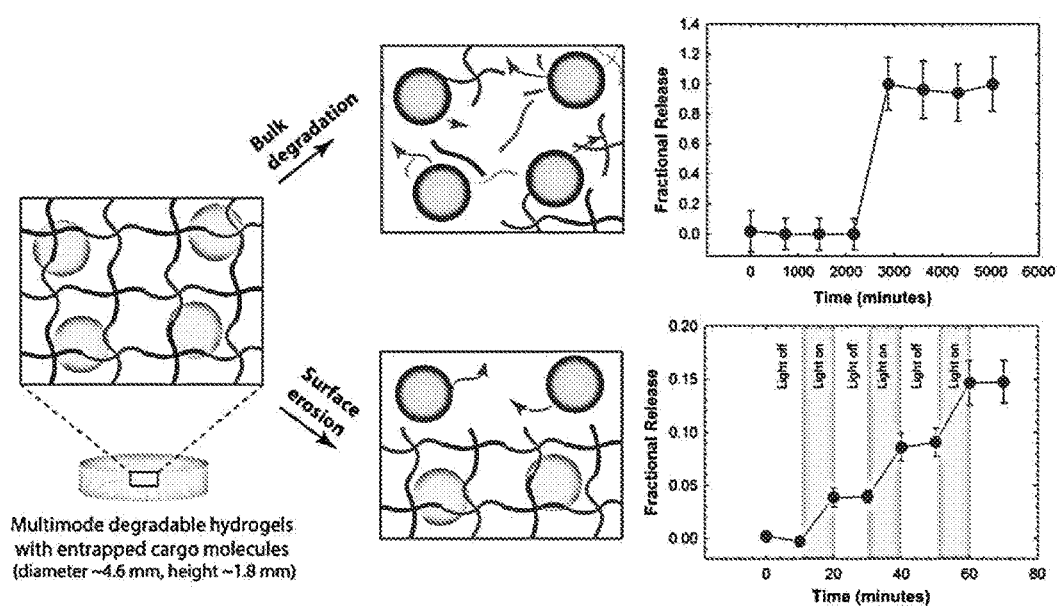
FIG. 4 shows in schematic form a multimode degradable hydrogel containing entrapped cargo substances and also shows the results of tests conducted using fluorescently labeled nanobeads, wherein the nanobeads were released from a hydrogel by a bulk degradation mechanism and a surface erosion mechanism (in response to externally applied light), as further described in the Examples.

To demonstrate the utility of this multimode degradable system for tailored release, fluorescently labeled nanobeads were entrapped within the hydrogel as a model cargo substance that can be laden with various therapeutics of interest and bead release was monitored using fluorescence spectroscopy. Since the diameter of these nanobeads (ø≈100 nm) is ~10-fold larger than the estimated mesh size of the hydrogels (ξ≈10 nm), it was hypothesized that the release of cargo substance would be driven by hydrogel degradation. The release of nanobeads in response to appropriate degradation stimuli was monitored in solution using fluorescence spectroscopy over the experiment time course. The fractional release was plotted as a function of time. As can be seen in FIG. 4, hydrogels that were incubated in a reducing microenvironment exhibited limited release of nanobeads before complete hydrogel dissolution, where release was observed only after reverse gelation. In contrast, hydrogels that were degraded using externally applied light exhibited light-responsive release with approximately 5% release of loaded cargo in response to each 10 minutes irradiation pulse (10 mW/cm$^2$ at 365 nm). These release profiles are consistent with the degradation mechanisms for the related functional groups, where multimode hydrogels should degrade in bulk with reducing and aqueous microenvironments and by surface erosion with applied light. Indeed, increasing hydrogel volume and swelling was observed over time when multimode degradable hydrogels were incubated in a reducing and aqueous microenvironment, indicating uniform cleavage of crosslinks throughout the hydrogel and a bulk degradation mechanism. For photodegradation studies, the height of the hydrogel decreased as a function of time while no significant changes in the diameter of hydrogel discs were observed, suggesting degradation by surface erosion and consistent with the observed fractional release of nanobeads in response to pulses of light. Surface erosion is expected when using UV and visible light to degrade these o-nitrobenzyl ether-based hydrogels, owing to the strong absorbance of these wavelengths of light by the photolabile group. Interestingly, the release of nanobeads (~5%) in response to each applied light pulse was less than expected based on values calculated release (~13%) based on the rate of surface erosion in degradation studies. Without wishing to be bound by theory, it is believed that this disparity likely arises from increased light attenuation in the presence of nanobeads (~17% by volume of total gel content) that scatter light and may hinder the light penetration through the full thickness of the hydrogel. Overall, these results support the hypothesis that the release of cargo can be tuned by controlling degradation rate. Such a strategy could be employed for spatiotemporal control over release of cargo molecules in biological systems.

What is claimed is:

1. A hydrogel comprising a three-dimensional network of polymeric segments, wherein the polymeric segments are linked together, at least in part, by at least one photodegradable moiety and at least one thioether-containing moiety obtained by reaction of a thiol with an α,β-unsaturated carbonyl functional group which is a maleimide functional group.

2. The hydrogel of claim 1, comprising a first polymeric segment which is linked to a second polymeric segment through a multimode degradable linkage comprised of a photodegradable moiety and a thioether-containing moiety obtained by reaction of a thiol with an α,β-unsaturated carbonyl functional group which is a maleimide functional group.

3. The hydrogel of claim 2, wherein the multimode degradable linkage is additionally comprised of a hydrolyzable ester or amide moiety.

4. The hydrogel of claim 1, wherein the polymeric segments include polyoxyalkylene-containing segments.

5. The hydrogel of claim 1, wherein the polymeric segments include polymeric segments selected from the group consisting of polyether-containing segments, polypeptide-containing segments, polysaccharide-containing segments and combinations thereof.

6. The hydrogel of claim 1, wherein the at least one photodegradable moiety includes at least one photodegradable moiety selected from the group consisting of nitro-substituted benzyl ester moieties and nitro-substituted benzyl amide moieties.

7. The hydrogel of claim 1, wherein the at least one photodegradable moiety includes at least one photodegradable moiety containing an ester or amide linkage in the backbone of the three-dimensional network that undergoes irreversible cleavage upon being irradiated with UV, visible or IR light.

8. The hydrogel of claim 1, wherein the at least one photodegradable moiety includes at least one photodegradable moiety having the general structure —Ar(NO$_2$)—CHR'—Z—C(=O)—, wherein Ar is an aromatic moiety substituted with a nitro group ortho to —CHR'—, Z is O or NH, and R' is H or alkyl.

9. The hydrogel of claim 1, wherein the polymeric segments are additionally linked together by at least one hydrolyzable moiety.

10. The hydrogel of claim 9, wherein the at least one hydrolyzable moiety includes at least one enzymatically-hydrolyzable moiety.

11. The hydrogel of claim 1, wherein the at least one thioether-containing moiety includes at least one thioether-containing moiety capable of undergoing a thiol exchange reaction.

12. The hydrogel of claim 11, wherein the at least one thioether-containing moiety capable of undergoing a thiol exchange reaction has the structural formula -A-S—R— where A is an aryl moiety or a heteroaromatic ring moiety and R is a succinimide moiety, the S being covalently bound to a carbon atom of the succinimide moiety.

13. The hydrogel of claim 1, wherein the thiol is an arylthiol.

14. The hydrogel of claim 1, wherein the polymeric segments are linked together, at least in part, by at least one moiety comprising structure (II):

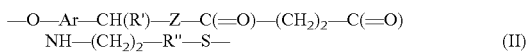
(II)

wherein Ar is a nitro-substituted aromatic ring, R' is H or alkyl, Z is O or NH, R" is a succinimide moiety having a nitrogen atom covalently bonded to —(CH$_2$)$_2$—, and S is covalently bound to R" through a carbon atom of the succinimide moiety.

15. The hydrogel of claim 1, wherein the polymeric segments of the hydrogel are linked together, at least in part, by at least one moiety comprising structure (III):

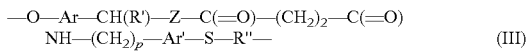
(III)

wherein Ar is a nitro-substituted aromatic ring, R' is H or alkyl, Z is O or NH, Ar' is an aromatic ring, p is an integer of 1 or more, R" is a succinimide moiety, and S is covalently bound to R" through a carbon atom of the succinimide moiety.

16. A composition, comprising the hydrogel of claim 1 with at least one cargo substance encapsulated therein and/or covalently bound to the three-dimensional network of the hydrogel.

17. The composition of claim 16, wherein the at least one cargo substance includes at least one bioactive substance.

18. The composition of claim 17, wherein the bioactive substance is selected from the group consisting of small molecule drugs, biomolecules, biomacromolecules and cells.

19. The composition of claim 16, wherein the cargo substance is a polymeric or inorganic particle.

20. The composition of claim 16, wherein the at least one cargo substance includes a cargo substance which is physically retained within the hydrogel.

21. The composition of claim 16, wherein the at least one cargo substance includes a cargo substance which is covalently bound to the three-dimensional network of the hydrogel.

22. A method of delivering a cargo substance to a subject in need thereof, wherein the method comprises administering a composition in accordance with claim 16 to the subject.

23. The method of claim 22, additionally comprising exposing at least a portion of the composition to light following administration of the composition to the subject.

24. The method of claim 22, wherein the composition is administered by injection, topical administration or implantation.

25. A method of making a hydrogel, wherein the method comprises reacting a functionalized polymer bearing at least x functional groups X with a functionalized linker molecule bearing at least y functional groups Y, wherein a) x and y are each independently an integer of 2 or more and x+y is an integer of 5 or more; b) X and Y are different from each other and are selected from the group consisting of maleimide and thiol, wherein one of X or Y is a malemide and one of X or Y is a thiol; c) at least one of the functionalized polymer or the functionalized linker molecule has a backbone containing at least one photodegradable moiety; and d) X and Y react to form a thioether linkage.

26. The method of claim 25, wherein the functionalized polymer is a functionalized polyether, functionalized polypeptide or functionalized polysaccharide.

27. The method of claim 25, wherein the photodegradable moiety includes at least one photodegradable moiety selected from the group consisting of nitro-substituted benzyl ester moieties and nitro-substituted benzyl amide moieties.

28. The method of claim 25, wherein the at least one photodegradable moiety includes at least one photodegradable moiety containing an ester or amide linkage that undergoes irreversible cleavage upon being irradiated with UV, visible or IR light.

29. The method of claim 25, wherein X and Y are selected from the group consisting of maleimide and arylthiol.

30. The method of claim 25, wherein the functionalized linker molecule is a polyether, polypeptide or polysaccharide bearing at least y functional groups Y.

31. The method of claim 25, wherein the functionalized polymer or the functionalized linker molecule corresponds to structure (I):

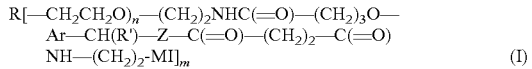
(I)

wherein R is an organic moiety, n is an integer of 2 or more, Ar is a nitro-substituted aromatic ring, R' is H or alkyl, Z is O or NH, MI is a maleimide moiety having a nitrogen atom covalently bonded to —(CH$_2$)$_2$— and m is an integer of 2 or more.

32. The method of claim 25, wherein the functionalized polymer or the functionalized linker molecule corresponds to structure (IV):

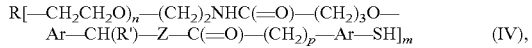
(IV), wherein R is an organic moiety, n is an integer of 2 or more, Ar is a nitro-substituted aromatic ring, R' is H or alkyl, Z is O or NH, Ar' is an aromatic ring, p is an integer of 1 or more, and m is an integer of 2 or more.

33. The method of claim 25, wherein at least one of the functionalized polymer or the functionalized linker molecule contains a bioactive moiety, which can be part of the backbone of the functionalized polymer or functionalized linker molecule or pendant to the backbone of the functionalized polymer or functionalized linker molecule.

34. The method of claim 25, wherein the reaction is carried out in the presence of at least one cargo substance, whereby the at least one cargo substance becomes encapsulated in the hydrogel formed.

* * * * *